United States Patent [19]

Hansen

[11] 4,221,220
[45] Sep. 9, 1980

[54] SURGICAL SUCTION APPARATUS

[76] Inventor: James Hansen, P.O. Box 136, Anaholo, Kauai, Hi. 96703

[21] Appl. No.: 870,918

[22] Filed: Jan. 19, 1978

[51] Int. Cl.² .............................................. A61M 1/00
[52] U.S. Cl. ..................................... 128/276; 433/95; 128/348
[58] Field of Search ............... 128/275, 276, 277, 278, 128/348, 350 R, 351; 32/33; 15/419, 420, 421

[56] References Cited

U.S. PATENT DOCUMENTS

| | | | |
|---|---|---|---|
| 3,321,087 | 5/1967 | Fuge et al. | 128/350 R |
| 3,430,631 | 3/1969 | Abramson | 128/350 R |
| 3,656,485 | 4/1972 | Robertson | 128/349 R |
| 3,807,401 | 4/1974 | Riggle et al. | 32/33 |
| 3,848,604 | 11/1974 | Sackner | 128/350 R |
| 3,945,385 | 3/1976 | Sackner | 128/276 |
| 3,960,153 | 6/1976 | Carey et al. | 128/350 R |
| 4,022,218 | 5/1977 | Riddick | 128/350 R |

FOREIGN PATENT DOCUMENTS 258116   3/1913   Fed. Rep. of Germany ...... 128/350 R

OTHER PUBLICATIONS

J. Thoracic & Cardiovascular Surg. vol. 57, No. 5, p. 24, May, 1969.

Webster's Seventh New Collegiate Dictionary G. C. Merriam Co., 1963, pp. 740 and 600 "Ridge" and oval.

Primary Examiner—William E. Kamm
Assistant Examiner—J. L. Kruter
Attorney, Agent, or Firm—James Creighton Wray

[57] ABSTRACT

A surgical suction nozzle for removing surgical debris and vomitus from unconscious patients in a surgical operative field that is highly resistant to clogging.

An oval-shaped opening forming the suction tip is circumscribed by a raised ridge inward of the opening. A plurality of small apertures inward of the raised ridge circumscribes the nozzle, which is placed into the mouth during surgery. The suction nozzle is angularly related in three cylindrical segments to prevent any encumbrance to the surgeon.

A suction control hole located on the medial segment of the suction nozzle allows the surgeon to control the suction pressure during the operation. The proximal end of the suction nozzle is beveled to be connected to a suction tube which transports surgical debris to a vacuum collection jar via a suction pipe in the cap of the jar. A debris removal pipe in the cap of the jar is connected to a vacuum tube leading to the vacuum line service outlet found in the surgery room.

2 Claims, 5 Drawing Figures

SURGICAL SUCTION APPARATUS

BACKGROUND OF THE INVENTION

1. Field of the Invention

The present invention relates generally to a surgical suction instrument for drawing off surgical debris from unconscious patients during surgery. The invention relates more specifically to the removal of vomitus from the mouths of patients during cardiopulmonary resuscitation.

2. Description of the Prior Art

Pertinent United States and foreign patent are found in Class 128, subclasses 275, 276, 277, 278, 297, 348, 350 R, 351; Class 15, subclasses 300 R, 415, 419, 420 and 421, the official classifications of the U.S. Patent and Trademark Office.

Examples of the most pertinent patents are U.S. Pat. Nos.: 2,253,143; 2,470,665; 3,460,255; 3,610,242; 3,807,401; 3,848,604; 3,885,567; 3,902,494; 4,022,218; and German Pat. No. 2,364,119.

U.S. Pat. No. 2,253,143 discloses a dental aspirator for the removal of secretions of the mouth, blood and other debris resulting from dental work.

U.S. Pat. Nos. 2,470,665 and 3,885,567 show a gastrointestinal fluid removal device inserted into the stomach or intestine in gastric analysis procedure. U.S. Pat. No. 3,885,567 comprises a double lumen for introducing as well as removing fluid and debris.

U.S. Pat. No. 3,460,255 shows a dental aspirator angularly cut to provide an intake zone and auxiliary openings through the wall of the aspirator.

U.S. Pat. No. 3,610,242 shows a vacuum suction system used to aspirate mucus from nose, mouth, pharynx, trachea or bronchi of patients. Suction pressure is controlled by a small aperture in the tube which is covered by the thumb.

U.S. Pat. No. 3,807,401 shows an anticoagulating blood suction device for use in intra-operative auto-transfusion operations which removes pools of blood and simultaneously introduces a controlled amount of anti-coagulant into the blood stream.

U.S. Pat. No. 3,848,604 and German Pat. No. 2,364,119 show a suction catheter comprising an elongated flexible plastic tube having a lumen running interiorly thereof and defining an opening at the distal end. The distal end of the tube is provided with a laterally extending flange and a plurality of apertures are defined immediately inward of the flange to produce a gas flow over the flange to provide a gaseous cushion between the flange and the wall of the body cavity.

U.S. Pat. No. 3,902,494 shows a surgical suction device comprising a suction shaft of an electrically insulating material and further comprising a coagulating electrode positioned at the suction port to prevent clogging of the suction shaft. The device is used for removing liquids and coagulating tissue from the operation area.

U.S. Pat. No. 4,022,218 shows a surgical suction tube comprising three separate sections, a tapering transparent plastic tube which forms the suction tip, a turbulence chamber having a circular cross-section tapered at both ends from a bulbous central section and a flexible plastic tube connected to a suction tube leading to the source of suction. Debris drawn into the turbulence chamber is prevented from clogging due to the air turbulence generated by the shape of the bulbous central portion of the chamber.

A number of problems remain in the prior art suction apparatus systems. None of the prior art discloses a suction opening at the distal end of greater than one-quarter inch, hardly adequate to remove partially chewed and digested chunks of solid food from the mouth and throat. None of the prior art discloses suction tubes large enough in diameter to allow large chunks of food to be easily transported into a vomitus collection jar with little clogging. Further, none of the prior art discloses a suction pipe and a vacuum pipe both embedded in the cap of the collection jar with differing diameters to allow the transference of large food chunks from the suction tube to the collection jar and connection to the vacuum line service outlet.

None of the prior art discloses any apertures in the suction nozzle to prevent the suction tip from applying too much pressure against the soft tissues of the mouth.

Further, none of the prior art discloses a compressed suction tip to allow the physician an unobstructed working area during surgery.

SUMMARY OF THE INVENTION

The present invention is an improvement over the prior art suction devices for the removal of vomitus from unconscious patients during surgery.

The present invention has an enlarged cap hole and suction pipe on the vomitus collection jar and an enlarged suction nozzle. The nozzle is a circular tube angularly bent at 30° to 40° angles forming three related segments. The nozzle is flattened at the distal end to form an oval which may be described as having parallel sides terminating in semi-circular ends. This allows the physician greater visibility into the oral cavity to effectively intubate the unconscious patient. Suction pressure is controlled by pressing a finger on a small aperture located on the medial segment of the nozzle.

A raised ridge around the tip of the nozzle protects several small air intake holes from occlusion by the soft tissues of the mouth. These small holes prevent the oval suction tip from inadvertently applying too much suction pressure and damaging sensitive mouth tissue.

The increased diameter of the suction tube and the oval opening of the suction nozzle overcomes the inadequacies of the prior art which suffer from repeated clogging due to small size. The forward bend in the suction nozzle on the distal end allows a convenient angle to insert the tip in the patient's mouth while keeping the operator's hand out of the way. The rear bend of the nozzle at the proximal end drops the rear of the nozzle and the attached suction tube out of the operator's way.

OBJECTS OF THE INVENTION

Objects of the invention are, therefore, to provide a suction nozzle with a large oval shaped suction hole, to provide a suction nozzle bent twice forming three angularly connected sections, to provide a raised ridge set slightly inward of the distal end, to provide a series of small holes adjacent to the ridge and circumscribing the nozzle and to provide a circular suction tube extending from the suction nozzle to a vomitus collection jar.

Another object of the invention is to provide an enlarged cap hole and suction pipe connected to the vomitus collection jar cap next to a conventional smaller size pipe and tube connected to the vacuum service line outlet.

Still another object of the invention is to provide a suction control aperture on the nozzle.

An object of the invention is the provision of a suction nozzle for connection to a suction tube of a vomitus collection system, having open proximal and distal segments respectively terminating in proximal and distal ends, wherein the proximal end is adapted to be connected to the suction tube and the distal end has an oval shaped entrance.

Another object of the invention is the provision of an aspirating nozzle having proximal and distal segments angularly connected to a medial segment.

Another object of the invention is the provision of an aspirating nozzle with proximal and distal segments connected by a medial segment which contains a suction control hole along its circumference of said medial segment.

A further object of the invention is the provision of an aspirating nozzle having a raised ridge which circumscribes a portion of a distal segment spaced slightly inward from the distal end.

Another object of the invention is the provision of an aspirating nozzle having a series of small holes which circumscribe a distal segment inwardly adjacent the raised ridge which is spaced inwardly from the distal end.

A further object of the invention in the provision of a relatively large diameter suction tube connected to the proximal end of a nozzle and connected to a relatively large diameter suction pipe in the cap of the vomitus collection jar and a relatively small diameter tube connected between a small diameter suction pipe in the cap of the vacuum collection jar and a vacuum service line outlet.

These and other further objects and features of the invention are apparent in the disclosure which includes the above and below specifications and claims and drawings.

DETAILED DESCRIPTION OF THE DRAWINGS

Figure 1:
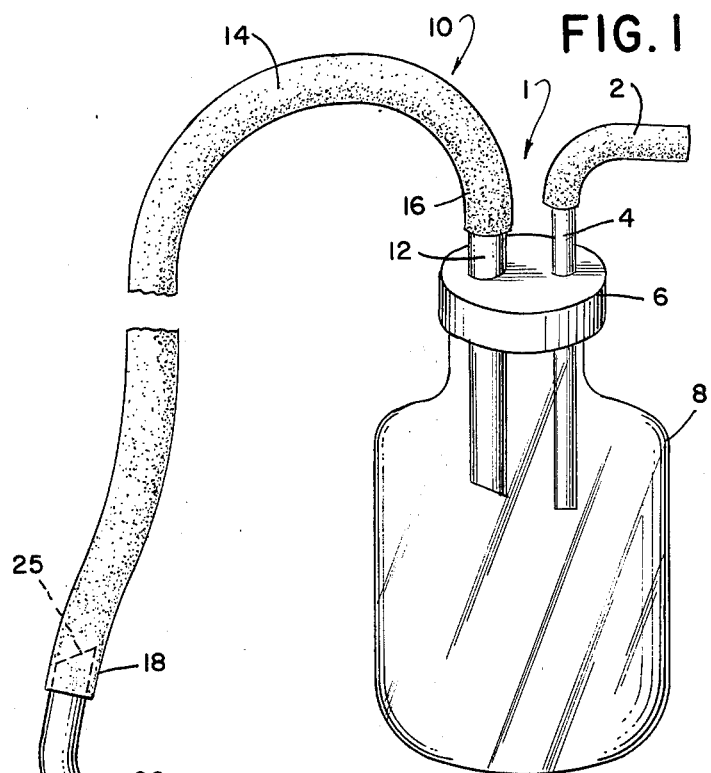
FIG. 1 is a schematic view of the suction device embodying the suction nozzle, suction tube, suction pipe, vomitus collection jar, and debris removal pipe and tube.

Referring to FIG. 1 a suction device 1 comprises a collection jar 8 for accumulating vomitus and other surgical debris, a cap cover 6 to which is connected a suction pipe 12 and a debris removal pipe 4. A debris removal tube 2 is connected to debris removal pipe 4. Suction pipe 12 facilitates the transference of vomitus from a suction tube 14 to collection jar 8. Debris removal pipe 4 transfers vomitus from collection jar 8 to debris removal tube 2.

A suction tube 14 is connected between a suction pipe 12 and a suction nozzle 20. Suction tube 14 transports vomitus from suction nozzle 20 to suction pipe 12 for disposal into collection jar 8 and suction nozzle 20 is beveled at proximal end 25 to facilitate the fit of suction tube 14.

Figure 2:
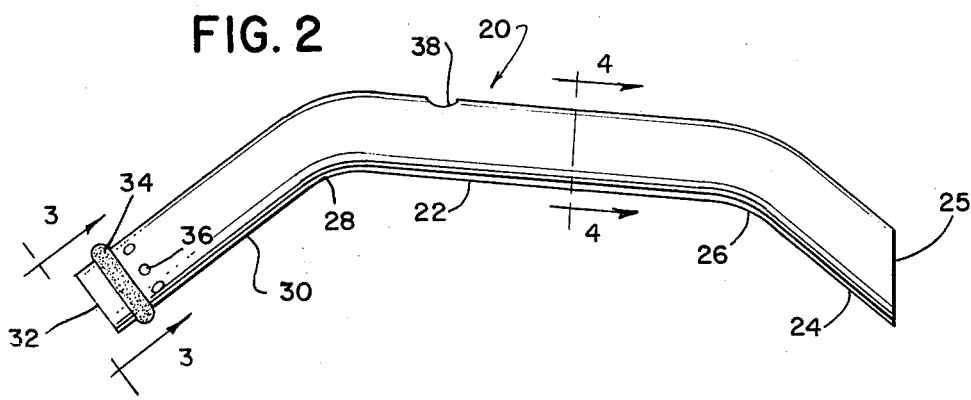
FIG. 2 is a lateral view of the suction nozzle with features raised ridge, air intake holes, angularly bent sections and suction control aperture.

Referring to FIG. 2 suction nozzle 20 is bent twice at 30° and 40° respectively forming three angularly related segments. Suction nozzle 20 is bent at distal end 28 in order to keep the nozzle 20 in the patient's mouth and to keep nozzle 20 out of the physician's way. Suction nozzle 20 is bent at proximal end 26 to prevent suction tube 14 from becoming entangled with the physician's hands during surgery.

Proximal segment 24 is beveled at proximal end 25 to fit the opening of suction tube 14 and also to provide a large egress for vomitus to pass out from suction nozzle 20 into suction tube 14 at suction tube entrance 18. Medial segment 22 contains suction control aperture 38 approximately 8 mm. in diameter. The suction aperture 38 allows the physician to regulate the suction pressure applied to the patient's mouth and throat. Distal segment 30 contains raised ridge 34 and a series of small air intake holes 36 approximately 3 mm. in diameter each which extend around the circumference of suction nozzle 20. These air intake holes 36 prevent the suction tip 32 from inadvertently applying too much pressure against the internal walls of the mouth by providing alternative suction pressure openings in the nozzle 20.

At the distal end of suction nozzle 20 is suction nozzle tip 32 compressed to form an oval shape. Suction of food chunks travel from suction tip 32 through suction nozzle 20 to suction tube 14.

Figure 3:
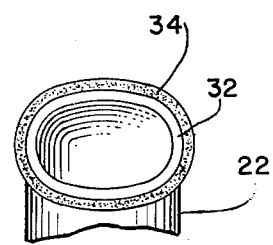
FIG. 3 is an end view of the suction nozzle at the distal end showing the oval shape and the raised ridge around the nozzle.

FIG. 3 is an end view of oval shaped suction tip 32. Suction tip 32 is oval shaped to increase the visibility and the working area inside the patient's mouth. The oval shaped tip allows the physician more room to insert an endotracheal tube into the patient's larynx to provide an air passageway during surgery. Raised ridge 34 circumscribes suction nozzle 20 at the distal end 30 approximately ¼" behind suction tip 32. Raised ridge 34 prevents the tissues of the mouth from occluding the air intake holes 36.

Suction tip 32 is approximately 25 mm. in width and 16 mm. in height and is connected to cylindrical medial segment 22 by distal segment 30 of suction nozzle 20.

Figure 4:
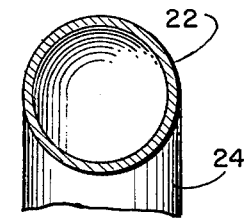
FIG. 4 shows an end view of the circular suction tube.

Referring to FIG. 4 medial segment 22 is connected to proximal end 24 of suction nozzle 20. The medial segment 22 is circular of approximately ¾" outer diameter and allows easy passage of food chunks through suction nozzle 20.

Figure 5:
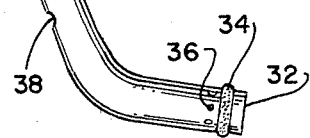
FIG. 5 shows a cross-sectional view of the collection jar cap with the suction pipe and vacuum pipe leading to and from the collection jar.
Figure 5:
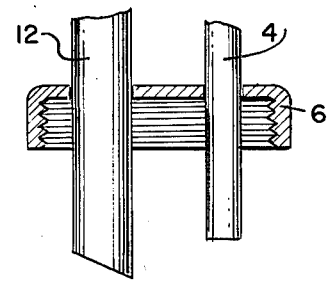

FIG. 5 shows a cross-sectional view of collection jar lid cover 6 containing suction pipe 12 of 11/16" inner diameter and vacuum pipe 4 of ⅜" inner diameter. Collection jar cap cover 6 screws onto collection jar 8 thrusting suction pipe 12 and debris removal pipe 4 into the middle of the aforementioned jar.

While the invention has been described with reference to a specific embodiment, the exact nature and scope of the invention is defined in the following claims.

What is claimed is:

1. A suction collection system comprising a one-piece hollow tube having proximal, medial and distal segments wherein the proximal and distal segments are angularly related to the medial segment; the proximal and medial segments have circular cross sections; the distal segment converges into an elliptical cross section terminating in an elliptical shaped entrance, a raised circumferential ring contiguous with the distal segment spaced slightly inward along the distal segment toward the medial segment from the elliptical shaped entrance of the distal segment,
a series of small circular apertures circumscribing the distal segment inwardly adjacent the raised circumferential ring,
a circular suction control aperture mounted along a circumference of the circular cross-section medial segment near an intersection of the medial and distal segments,
a large diameter suction tube connected to a proximal end of a section nozzle and connected to a large diameter suction pipe in a cap of a vomitus collection system and a smaller diameter tube connected between a smaller diameter suction pipe in the cap of the vomitus collection system and a vacuum service outlet.

2. The suction collection system of claim 1 wherein a portion of the proximal segment adjacent the proximal end is beveled to be adapted to be connected to the suction tube of the vomitus collection system.

* * * * *

UNITED STATES PATENT AND TRADEMARK OFFICE
Certificate

Patent No. 4,221,220                 Patented September 9, 1980

James Hansen

Application having been made by James Hansen the inventor named in the patent above-identified, for the issuance of a certificate under the provisions of Title 35, Section 256, of the United States Code, adding the name of Terry R. Howard as a joint inventor, and a showing and proof of facts satisfying the requirements of the said section having been submitted, it is this 29th day of May 1984, certified that the name of the said Terry R. Howard is hereby added to the said patent as a joint inventor with the said James Hansen.

Fred W. Sherling,
*Associate Solicitor.*